United States Patent [19]

Takano et al.

[11] Patent Number: 5,233,056

[45] Date of Patent: Aug. 3, 1993

[54] OPTICALLY ACTIVE CHROMAN DERIVATIVES AND INTERMEDIATES THEREOF, AND PROCESS FOR MANUFACTURING SAME

[75] Inventors: Seiichi Takano; Kunio Ogasawara, both of Sendai, Japan

[73] Assignee: Asahi Denka Kogyo K.K., Tokyo, Japan

[21] Appl. No.: 789,533

[22] Filed: Nov. 8, 1991

Related U.S. Application Data

[62] Division of Ser. No. 641,675, Jan. 16, 1991, abandoned.

[30] Foreign Application Priority Data

Jan. 18, 1990 [JP] Japan ......................................... 2-9157

[51] Int. Cl.⁵ ............................................. C07D 311/58
[52] U.S. Cl. ..................... 549/407; 549/360; 549/417
[58] Field of Search .......................................... 549/407

[56] References Cited

U.S. PATENT DOCUMENTS 4,424,389  1/1984  Sakito ................................... 549/407
4,645,845  2/1987  Gehrken et al. .................... 549/407

Primary Examiner—Nicky Chan
Attorney, Agent, or Firm—Sherman and Shalloway

[57] ABSTRACT

An optically active (S)- or (R)-chroman-2-ethanol compound of a general formula (I)

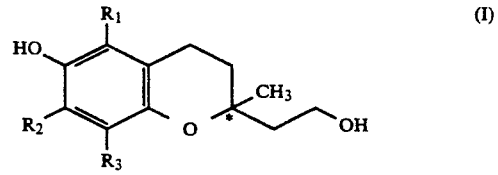

wherein $R_1$, $R_2$ and $R_3$ independently represent a hydrogen atom or a lower alkyl group having 1 to 4 carbon atoms, and a chiral central carbon atom marked with a symbol * in the formula (I) alternatively has one of an R-configuration and an S-configuration, is disclosed. Further, intermediate products of the compound of the formula (I) are also disclosed. Still further, a process for manufacturing the above compounds is disclosed. The compound of the formula (I) is easily synthesized from an easily available optically active starting material.

10 Claims, No Drawings

OPTICALLY ACTIVE CHROMAN DERIVATIVES AND INTERMEDIATES THEREOF, AND PROCESS FOR MANUFACTURING SAME

This application is a division of application Ser. No. 07/641,675, filed Jan. 16, 1991, now abandoned.

BACKGROUND OF THE INVENTION

1. Field of the Invention

The present invention relates to an optically active novel compound and intermediate products thereof, and a process for the manufacture of same.

2. Description of the Related Art

Vitamin E is a methylated derivative of a tocopherol, and includes eight kinds of naturally occurring compounds, i.e., α-, β-, γ-, and δ -tocopherols, and α-, β-, γ-, and δ -tocotrienols. Although tocopherols and tocotrienols include d-form, l-form or dl-form optical isomers, naturally occurring compounds have optical activities. Synthesized tocopherols are generally prepared in the form of a diastereomer, and it is known that a chirality of the carbon atom of the 2-position in the chroman ring has a considerable affect on physiological activities of tocopherols.

A method of synthesizing optically active tocopherols from optically active starting materials is described in, for example, N. Cohen, et al, Journal of the American Chemical Society, 101:22, Oct. 24, 1979, 6710–6716. In the method of Cohen, et al, an optically active desired α-tocopherol is obtained by using an optically active benzopyran derivative as a starting material, to form an optically active chroman-2-methanol derivative, and then performing a Wittig coupling of the chroman derivative to form the final α-tocopherol while retaining the chirality of the starting material. In this method, however, a resolution process is required to obtain the optically active starting material, and a poisonous hydrocyanic acid must be used during the course of the synthesis process.

SUMMARY OF THE INVENTION

Accordingly, an object of the present invention is to provide intermediates from which naturally occurring or non-occurring tocopherols can be alternatively prepared, without the need for a resolution process and the need of poisonous reagents, and which can be prepared from an easily available starting material having an optical activity.

Other objects and advantages of the present invention will be apparent from the following description.

In accordance with the present invention, there is provided an optically active (S)- or (R)-chroman-2-ethanol compound of a general formula (I)

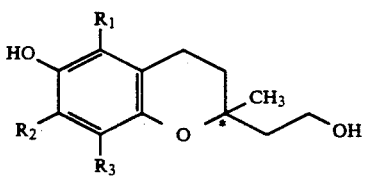

wherein $R_1$, $R_2$ and $R_3$ independently represent a hydrogen atom or a lower alkyl group having 1 to 4 carbon atoms, and a chiral central carbon atom marked with a symbol * in said formula (I) alternatively has one of an R-configuration and an S-configuration.

Further, in accordance with the present invention, there is provided an optically active (S)- or (R)-phenylpentanetriol compound of a general formula (V)

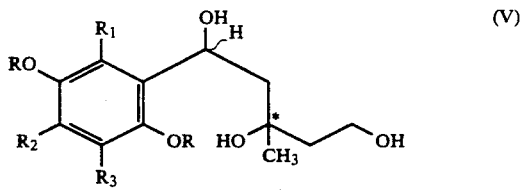

wherein R represents a group for protecting a hydroxy group, and $R_1$, $R_2$, $R_3$ and the symbol * have the same meanings as above.

Still further, in accordance with the present invention, there is provided an optically active (S)- or (R)-quinonepentanetriol compound of a general formula (VI)

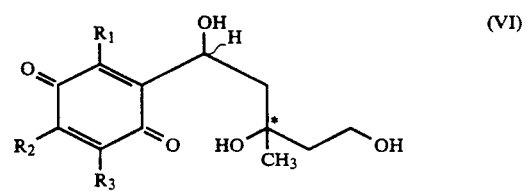

wherein $R_1$, $R_2$, $R_3$ and the symbol * have the same meanings as above.

Still further, in accordance with the present invention, there is also provided an optically active tricyclic benzoquinone monoketal compound of a general formula (VII)

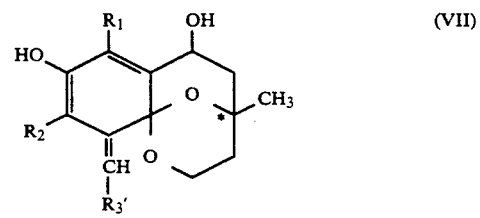

wherein $R_3'$ represents a member necessary to form a group $R_3$ together with the group —CH— and the hydrogen atom H in said formula (VII), and $R_1$, $R_2$, $R_3$ and the symbol * have the same meanings as above.

Still further, in accordance with the present invention, there is provided a process for manufacturing the above compounds.

DESCRIPTION OF THE PREFERRED EMBODIMENTS

The process for manufacturing the compounds of the present invention includes the following steps.

(a) A step comprising reducing an optically active (S)- or (R)-mevalonolactone of a formula (II):

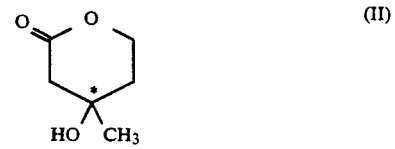

to obtain an optically active corresponding (S)- or (R)-mevalonolactol of a formula (III):

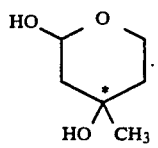

(b) A step comprising reacting the lactol of the formula (III) and a benzene magnesium halide of a formula (IV):

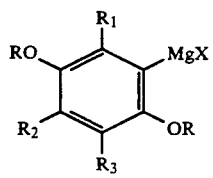

wherein R represents a group for a protecting hydroxy group, preferably a lower alkyl group having 1 to 4 carbon atoms and optionally substituted with one or more lower alkoxy groups having 1 to 4 carbon atoms (such as methyl, methoxymethyl or methoxyethoxymethyl), a benzyl or substituted benzyl group, a substituted phenyl group (such as p-methoxyphenyl), or a silyl group substituted with one or more lower alkyl groups having 1 to 4 carbon atoms (such as t-butyldimethylsilyl), $R_1$, $R_2$ and $R_3$ independently represent a hydrogen atom or a lower alkyl group having 1 to 4 carbon atoms, preferably a methyl or ethyl group, and X represents a halogen atom, preferably a bromine or iodine atom, to thereby obtain an optically active corresponding (S)- or (R)-phenylpentanetriol compound [hereinafter optionally referred to as phenyltriol compound] of a formula (V)

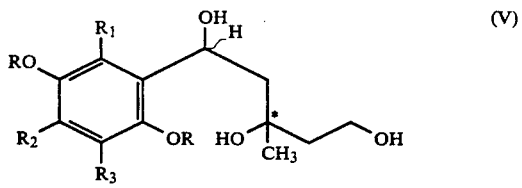

while retaining the S-configuration or R-configuration alternatively possessed by the chiral central carbon atom. In the phenyltriol compound (V) obtained in this step, a configuration of another chiral central carbon atom combined with the phenyl group is not necessarily alternative but may be in the form of an SR mixture.

(c) A step comprising removing protecting groups R from the phenyltriol compound (V), to thereby obtain an optically active corresponding (S)- or (R)-quinonepentanetriol compound [hereinafter optionally referred to as benzoquinonetriol compound] of a formula (VI):

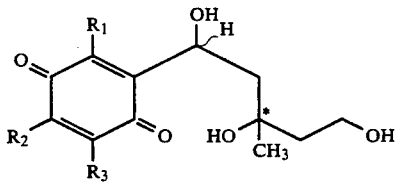

wherein $R_1$, $R_2$, $R_3$ and the symbol * have the same meanings as above, while retaining the S-configuration or R-configuration alternatively possessed by the chiral central carbon atom. In the benzoquinonetriol compound (VI) obtained in this step, a configuration of another chiral central carbon atom combined with the benzoquinone group is not necessarily alternative but may be in the form of an SR mixture.

(d) A step comprising cyclizing the benzoquinonetriol compound (VI), to thereby obtain an optically active corresponding tricyclic quinone monoketal compound [hereinafter optionally referred to as benzoquinone monoketal compound] of a formula (VII):

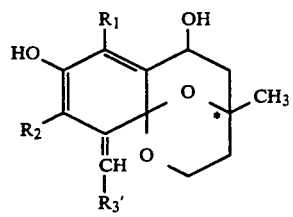

wherein $R_3'$ represents a member necessary to form a group $R_3$ together with the group —CH— and the hydrogen atom H in said formula (VII), and $R_1$, $R_2$, $R_3$ and the symbol * have the same meanings as above, while retaining the S-configuration or R-configuration alternatively possessed by the chiral central carbon atom. In the benzoquinone monoketal compound (VII) obtained in this step, a configuration of another chiral central carbon atom combined with the hydroxy group in the oxane ring is not necessarily alternative but may be in the form of an SR mixture.

(e) A step comprising treating the benzoquinone monoketal compound (VII) under a hydrogenolysis condition, to thereby obtain the optically active corresponding (S)- or (R)-chroman-2-ethanol compound [hereinafter optionally referred to as chroman ethanol compound] of the formula (I), while retaining the S-configuration or R-configuration alternatively possessed by the chiral central carbon atom.

The steps (a) to (e) will be described hereinafter in detail.

Step (a)

The starting mevalonolactone (II) contains a chiral center, and thus includes an S-form and an R-form. Each of mevalonolactones (II) in the S-form and the R-form may be prepared by the known process described in, for example, Japanese Unexamined Patent Publication No. 60-146840. When mevalonolactone (II) in the S-form or the R-form is reduced with a metal hydride reducing agent, preferably an aluminum hydride reducing agent, more preferably a dialkyl aluminum hydride (such as dibutyl aluminum hydride, or trialkoxy lithium aluminum hydride), in an atmosphere of an inert gas (such as an argon or nitrogen gas) and at a low temperature (such as 0° C. to −78° C., preferably −10° C. to −78° C.), in an anhydrous aprotic solvent (such as tetrahydrofuran, toluene, hexane or ether), the desired mevalonolactol (III) is obtained as a waxy solid while retaining an unchanged chirality, in a substantially pure form which may be used in a subsequent step without purification.

Step (b)

The optically active mevalonolactol (III) obtained in the above step (a) is gradually added at a low temperature of about 0° C. to −20° C. to the magnesium halide compound (IV) which has been previously prepared in an organic solvent (for example, ether, tetrahydrofuran or dioxane) in an atmosphere of an inert gas (such as an argon or nitrogen gas). After a reaction at about 0° C. to a room temperature is completed, the phenyltriol compound (V) is obtained as an oil while retaining the chirality stemming from the mevalonolactol (III). The pentane chain of the phenyltriol compound (V) includes 2 chiral central carbon atoms, i.e., (a) the chiral central carbon atom stemming from the starting mevalonolactol compound (III), and (b) a chiral central carbon atom which is newly formed by the reaction of the mevalonolactol (III) and the magnesium halide compound (IV) and which is combined with the phenyl group. The configuration of the former chiral central carbon atom (a) is maintained in the step (b). The configuration of the latter chiral central carbon atom (b) is not alternative but may be in the form of an epimer mixture of about 1:1.

The resulting compound may be used in the subsequent step, after purification (for example, by silica gel column chromatography) if necessary.

Step (c)

The benzoquinone triol compound (VI) is obtained as an oil, while retaining an unchanged chirality, by removing the protecting group R from the phenyltriol compound (V) prepared in the above step (b), in an atmosphere of an inert gas (such as an argon or nitrogen gas), at an ordinary temperature, and in an aqueous-organic solvent preferably water-containing acetonitrile, water-containing tetrahydrofuran or water-containing dioxane, with an oxidizing agent, such as cerium (IV) salts, preferably ammonium cerium nitrate. The pentane chain of the resulting benzoquinone triol compound (VI) includes 2 chiral central carbon atoms stemming from the phenyltriol compound (V), wherein the configuration of the chiral central carbon atom (a) stemming from the starting mevalonolactol (III) is still retained in this step, and the configuration of the chiral central carbon atom (b) which is newly formed in the step (b) is still in the form of an epimer mixture of about 1:1.

The resulting compound may be used in the subsequent step, after purification (for example, by silica gel column chromatography) if necessary.

Step (d)

The benzoquinonetriol (VI) is cyclized by an intramolecular dehydration caused by a refluxing in dioxane in the presence of a catalytic amount of sulfuric acid, to thereby obtain the tricyclic benzoquinone monoketal (VII) while retaining the chirality. In the resulting compound (VII), the configuration of the chiral central carbon atom (a) stemming from the starting mevalonolactol (III) is still retained in this step, and the configuration of the chiral central carbon atom (b), which is newly formed in the step (b) is still in the form of an epimer mixture of about 1:1. The resulting compound may be used in the subsequent step without purification, but if purification is necessary, then silica gel column chromatography is used.

Step (e)

When the tricyclic benzoquinone monoketal (VII) is treated under a hydrogenolysis condition, the chroman-ethanol compound (I) is obtained while retaining the chirality stemming from the starting mevalonolactol (III). The resulting compound may be used in the subsequent step, after purification if necessary. The purification is carried out by silica gel column chromatography.

The chroman-ethanol compound (I) in the form of a racemic modification is known, but the optically active compounds of the S-form and R-form can not be obtained unless resolution procedure is used. The tocopherol having a naturally occurring form (i.e., R-form), which may be prepared from the chroman-ethanol compound (I) according to the present invention, exhibits a far greater physiological activity than that having the S-form.

An optically active tocopherol compound can be prepared from the optically active chroman ethanol compound (I) according to the present invention, while retaining the chirality thereof, by effecting a benzylation of the phenolic hydroxy group in the chroman-ethanol compound (I), then a tosylation of an active hydroxy group, and thereafter, a coupling of Grignard reagent to the tosylated side chain to introduce a side chain of tocopherol, and finally, a removal of the benzyl group on the phenolic hydroxy group.

According to the present invention, novel intermediate are provided, which may be prepared from an easily available mevalonolactone having an optical activity, and from which tocopherols having either a naturally occurring or non-occurring configuration can be alternatively synthesized. The intermediate compound according to the present invention are useful as an intermediate for various antioxidizing agents. Further, the intermediate compound of the present invention can be easily and safely prepared, because neither a resolution procedure nor poisonous reagents are required in the process for the manufacture thereof.

EXAMPLES

The present invention now will be further illustrated by, but is by no means limited to, the following Examples.

EXAMPLE 1

Preparation of 2ξ-hydroxy-(4R)-mevalonolactol

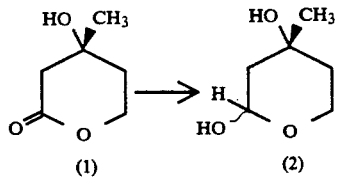

In an atmosphere of an argon stream, a toluene solution (1.5 ml: 2.7 mmol) of 1.8M diisobutylaluminum hydride was gradually added at −30° C. to a tetrahydrofuran solution (4 ml) containing 211 mg (1.62 mmol) of (R)-(+)-mevalonolactone (1). The reaction mixture was stirred at −30° C. for 45 minutes, quenched with 10% aqueous sodium hydroxide solution, stirred again at a room temperature for 1 hour, and then filtered with celite. Thereafter, the solvent was evaporated from the resulting filtrate to obtain an oily product. Further, the above celite used for the filtration was extracted overnight with ethyl acetate to obtain an oily product. These oily products were combined and treated with silica gel column chromatography, and from the ethyl acetate effluent, 180 mg (85%) of the above-mentioned compound (2) was obtained as a colorless oil.

Mass analysis (m/e): 132 (M+), 68 (100%).

IR (neat) cm$^{-1}$: 3300.

$^1$H-NMR (CDCl$_3$) δ: 4.9–5.39 (1H, m), 4.4–3.5 (2H, m), 4.6 and 3.25 (2H, brd and brd), 2.0–1.4 (4H, m), 1.3, 1.25 (3H, s×2).

EXAMPLE 2

Preparation of (3R)-1-(2,5-dimethoxy-3,4,6-triphenyl)-3-methyl-pentane-1ξ,3,5-triol

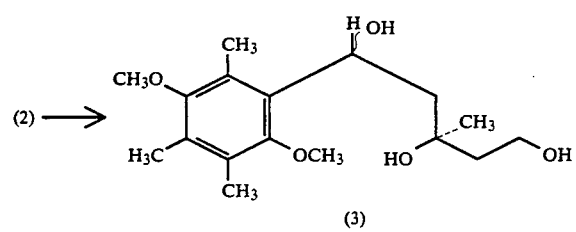

In an atmosphere of an argon stream, 1.1 g (0.045 mol) of magnesium, one drop of methyl iodide, and a catalytic amount of iodine were added to 30 ml of tetrahydrofuran, and further, a solution of 10.4 g (0.04 mol) of 2,5-dimethoxy-3,4,6-trimethyl-bromobenzene in 15 ml of tetrahydrofuran was added dropwise over 40 minutes while refluxing the tetrahydrofuran. The reaction was completed by refluxing for further 30 minutes, to thereby form 2,5-dimethoxy-3,4,6-trimethybenzene magnesium bromide. Then, after cooling to 0° C., 580 mg (4.4 mmol) of the lactol compound (2) prepared in Example 1 was added and stirred at a room temperature for 2 hours, an aqueous sodium bicarbonate saturated solution was added to the reaction mixture, and an extraction with diethyl ether was carried out. The organic phase was washed with an aqueous sodium chloride saturated solution, and dried over anhydrous magnesium sulfate, the solvent was evaporated under a reduced pressure, and the residue was treated by silica gel column chromatography. Then, 1.35 g (98.5%) of the above-mentioned compound (3) was obtained from the ethyl acetate effluent as a colorless oil.

Mass analysis (m/e): 312 (M+), 209 (100%).

IR (neat) cm$^{-1}$:3370.

$^1$H NMR (CDCl$_3$) δ: 5.45 (2H, m), 4.90 (2H, m), 4.25–3.60 (8H, m), 2.4–2.1 (9H, m), 1.85–1.5 (4H, m), 1.5 and 3.2 (3H, s×2).

EXAMPLE 3

Preparation of (3R)-1-(3,6-dioxo-2,4,5-trimethylcyclohexadiene-1,4)-3-methyl-pentane-1ξ,3,5-triol

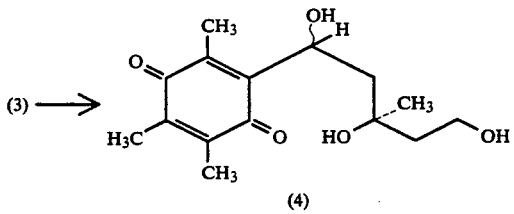

In an atmosphere of an argon stream, 1.3 g (4.17 mmol) of the triol compound (3) prepared in Example 2 was dissolved in 30 ml of acetonitrile and 30 ml of H$_2$O, and 11.27 g (33.4 mmol) of cerium (IV) ammonium nitrate was added at a room temperature. After stirring for 5 minutes, H$_2$O was added, and the reaction mixture was extracted with dichloromethane, washed successively with an aqueous sodium bicarbonate saturated solution and an aqueous sodium chloride saturated solution, and then dried over anhydrous magnesium sulfate. The solvent was evaporated under a reduced pressure, and the residue was treated by silica gel column chromatography, and 750 mg (64 %) of the above-mentioned compound (4) was obtained from the ethyl acetate/benzene (1:4) effluent as a colorless oil.

Mass analysis (m/e): 264 (—H$_2$O), 179 (100%).

IR (neat) cm$^{-1}$: 3350, 1720, 1640.

$^1$H-NMR (CDCl$_3$) δ: 5 (1H, m), 4.7–3.7 (5H, m), 2.4–2.0 (11H, m), 1.9–1.6 (2H, m), 1.5 and 1.3 (3H, s×2).

EXAMPLE 4

Preparation of 6,8-dihydroxy-10-methylene-4,7,9-trimethyl-2,3,4,5,6,10,10a-heptahydro-1-benzocine

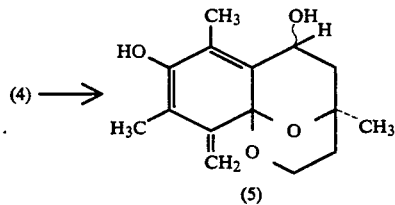

In an atmosphere of an argon stream, 345 mg (1.22 mmol) of the benzoquinone compound (4) prepared in Example 3 was dissolved in 12 ml of dioxane, and 2 ml of 2N sulfuric acid was added. After refluxing for 3 hours, the reaction mixture was cooled to a room temperature, diethyl ether and an aqueous sodium bicarbonate saturated solution were added, and the reaction mixture was extracted with diethyl ether, washed with an aqueous sodium chloride saturated solution, and then dried over anhydrous magnesium sulfate. The solvent was evaporated under a reduced pressure to obtain the above-mentioned compound (5), which was used in the next step without purification.

Mass analysis (m/e): 264 (M+), 201 (100%).

IR (neat) cm$^{-1}$: 3350.

$^1$H-NMR (CDCl$_3$) δ: 7.0 (brs, 1H), 5.05–4.7 (3H, m), 3.8–3.3 (2H, m), 2.9 (brs, 1H), 2.18 (3H, s), 2.12 (3H, s), 1.9–1.6 (4H, m), 1.39 (3H, s).

EXAMPLE 5

Preparation of (S)-(−)-6-hydroxy-2,5,7,8-tetramethylchroman-2-ethanol

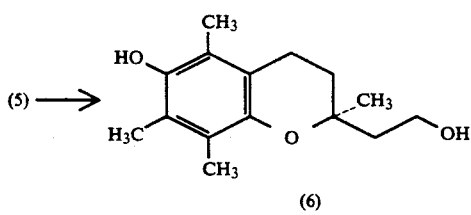

In an atmosphere of a hydrogen stream, the crude tricyclic ketal compound (5) prepared in Example 4 was dissolved in 10 ml of methyl alcohol, and 30 mg of palladium (II) hydroxide and 5 drops of trichloromethane were added. The reaction mixture was stirred at a room temperature for 3 days, filtered with celite. The solvent was evaporated under a reduced pressure, and the residue was treated by silica gel column chromatography. Then, 215 g (70%) of the above-mentioned compound (6) was obtained from the ether/hexane (1:2) effluent as a brown solid, and after recrystallization from dichloromethane/hexane, a colorless crystal was obtained.

Mass analysis (m/e): 250 (M+), 164 (100%).

IR (neat) cm$^{-1}$: 3400.

$^1$H-NMR (CDCl$_3$) δ: 4.7 (1H, brs), 3.90 (2H, t, J=7 Hz), 2.66 (2H, t, J=7 Hz), 2.16 (3H, s), 2.10 (6H, s), 1.7–2.2 (4H, m), 1.28 (3H, s).

[α]$D^{27}$= −4.06 (c=0.7, methyl alcohol).

Melting point: 137°–138° C.

Although the present invention has been described with reference to specific embodiments, various changes and modifications obvious to those skilled in the art are deemed to be within the spirit, scope and concept of the invention.

We claim:

1. A process for manufacturing an optically active (S) or (R) -chroman-2-ethanol compound of the general formula (I):

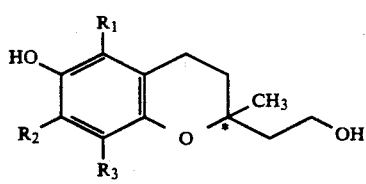

wherein R$_1$ and R$_2$ independently represent a hydrogen atom or a lower alkyl group having 1 to 4 carbon atoms, and a chiral central carbon atom marked with a symbol * in said formula (I) alternatively has one of an R-configuration and an S-configuration, said process comprising treating, under a hydrogenolysis condition, an optically active tricyclic benzoquinone monoketal compound of the general formula (VII):

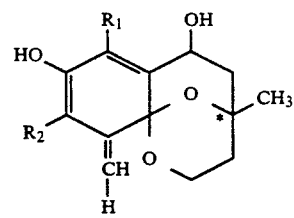

wherein R$_1$ and R$_2$ and the symbol * in said formula (VII) are as defined above, to obtain the corresponding optically active (S) - or (R) -chroman-2-ethanol compound of the general formula (I) while retaining the R-configuration or S-configuration of the chiral central carbon atom marked with the symbol * in said formula (VII).

2. The process according to claim 1, which further comprises preparing said optically active tricyclic benzoquinone monoketal compound of the general formula (VII) by cyclizing an optically active (S)- or (R)-quinonepentanetriol compound of the general formula (VI):

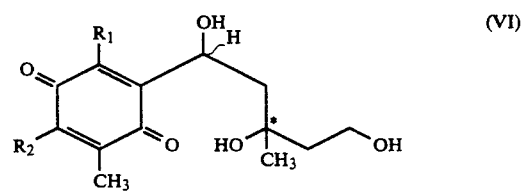

wherein R$_1$, R$_2$ and the symbol * have the same meanings as above.

3. The process according to claim 2, which further comprises preparing the optically active (S)- or (R) quinonepentanetriol compound of the general formula (VI) by removing the R groups for protecting hydroxyl groups, from an optically active (S)- or (R)-phenylpentanetriol compound of the general formula (V):

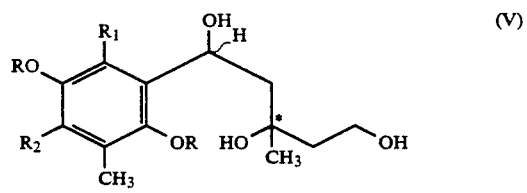

wherein each R represents a group for protecting a hydroxyl group, and R$_1$, R$_2$, and the symbol * have the same meaning as above.

4. The process according to claim 3, which further comprises preparing the optically active (S) or (R)-phenylpentanetriol compound of formula (V) by reacting an optically active (S)- or (R)-mevalonolactol compound of the formula (III):

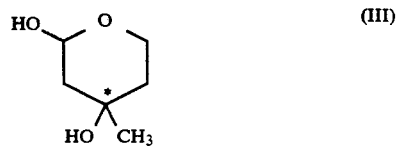

and a benzene magnesium halide of the general formula (IV):

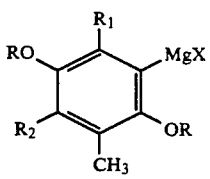
(IV)

wherein R, $R_1$, $R_2$, and the symbol * have the same meaning as above and X represents a halogen atom.

5. The process according to claim 4, which further comprises preparing the optically active (S)- or (R)-mevalonolactol compound of the formula (III), by reducing an optically active (S)- or (R)-mevalonolactone of the formula (II):

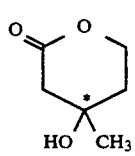
(II)

wherein the symbol * has the same meaning as above.

6. The process according to claim 5, wherein the optically active (S)- or (R)-mevalonolactone of the formula (II) is reduced with a metal hydride reducing agent.

7. The process according to claim 6, wherein the metal hydride reducing agent is a dialkyl aluminum hydride.

8. The process according to claim 3, wherein the R groups are removed with an oxidizing agent.

9. The process according to claim 8, wherein said oxidizing agent is a cerium (IV) salt.

10. The process according to claim 2, wherein said optically active (S)- or (R)-quinonepentanetriol compound of the general formula (VI) is cyclized by refluxing the compound in dioxane in the presence of a catalytic amount of sulfuric acid.

* * * * *